United States Patent
Nakata et al.

(10) Patent No.: US 7,309,313 B2
(45) Date of Patent: Dec. 18, 2007

(54) VASCULAR DISEASE EXAMINING SYSTEM AND BYPASS VASCULAR DIAGNOSING DEVICE

(75) Inventors: Kin-ichi Nakata, Tokyo (JP); Yoshiyuki Sankai, Ibaraki (JP)

(73) Assignees: Nihon University, Tokyo (JP); Tsukuba Technology Seed Co., Ltd., Ibaraki (JP)

( * ) Notice: Subject to any disclaimer, the term of this patent is extended or adjusted under 35 U.S.C. 154(b) by 20 days.

(21) Appl. No.: 10/481,104

(22) PCT Filed: Jun. 21, 2002

(86) PCT No.: PCT/JP02/06238

§ 371 (c)(1),
(2), (4) Date: Jun. 30, 2004

(87) PCT Pub. No.: WO03/000130

PCT Pub. Date: Jan. 3, 2003

(65) Prior Publication Data

US 2004/0243006 A1 Dec. 2, 2004

(30) Foreign Application Priority Data

Jun. 21, 2001 (JP) .............................. 2001-188032
Aug. 31, 2001 (JP) .............................. 2001-262965

(51) Int. Cl.
*A61B 5/02* (2006.01)
*A61B 8/00* (2006.01)
*A61B 5/00* (2006.01)

(52) U.S. Cl. ...................... 600/504; 600/300; 600/454

(58) Field of Classification Search ................... None
See application file for complete search history.

(56) References Cited

U.S. PATENT DOCUMENTS

| | | | | |
|---|---|---|---|---|
| 4,442,845 A | * | 4/1984 | Stephens | 600/500 |
| 4,677,984 A | * | 7/1987 | Sramek | 600/494 |
| 5,406,952 A | * | 4/1995 | Barnes et al. | 600/485 |
| 5,715,826 A | * | 2/1998 | Horrocks et al. | 600/485 |
| 6,045,510 A | * | 4/2000 | Ogura et al. | 600/485 |
| 6,171,242 B1 | * | 1/2001 | Amano et al. | 600/423 |
| 6,261,235 B1 | * | 7/2001 | Amano et al. | 600/485 |
| 6,315,735 B1 | * | 11/2001 | Joeken et al. | 600/500 |

(Continued)

FOREIGN PATENT DOCUMENTS

EP    0 638 281 A    2/1995

(Continued)

*Primary Examiner*—Max F. Hindenburg
*Assistant Examiner*—Patricia Mallari
(74) *Attorney, Agent, or Firm*—Sughrue Mion, PLLC

(57) ABSTRACT

Disclosed are a vascular disease examination system capable of examining and diagnosing vascular diseases such as arterial obliteration by determining the feature quantities of blood flow velocity waveforms or blood pressure waveforms or blood flow rates, and a bypass vascular diagnosing system. A blood flow velocity or blood pressure at a target location of the body is measured A waveform analysis unit 4 determines the feature quantity of a blood flow waveform (or blood pressure waveform), for displaying on an output unit 5. The feature quantity includes a time constant, Fourier transform value, differentiated value, integrated value, rise/fall time, and sharpness or gradient of rise. Feature quantity of a blood flow velocity waveform (or blood pressure waveform) indicated in numeric value enables a correct examination/diagnosis.

2 Claims, 14 Drawing Sheets

U.S. PATENT DOCUMENTS 6,485,431 B1 * 11/2002 Campbell ................... 600/526
6,524,257 B2 * 2/2003 Ogura ........................ 600/490

FOREIGN PATENT DOCUMENTS

| | | |
|---|---|---|
| JP | 7-95966 A | 4/1995 |
| JP | 11-113863 A | 4/1999 |
| JP | 11-505444 A | 5/1999 |
| JP | 11-309120 A | 11/1999 |
| JP | 2000-37358 A | 2/2000 |
| JP | 2001-8907 A | 1/2001 |
| JP | 2001-61956 A | 3/2001 |
| WO | WO 98/14119 A | 4/1998 |

\* cited by examiner

Prior to the bypass surgery

US 7,309,313 B2

VASCULAR DISEASE EXAMINING SYSTEM AND BYPASS VASCULAR DIAGNOSING DEVICE

TECHNICAL FIELD

The present invention relates to a vascular disease examination system and a bypass vascular diagnosing system capable of examining and diagnosing vascular diseases such as ischemic disease based on the blood flow velocity waveforms, blood pressure waveforms or blood flow rate waveforms.

DESCRIPTION OF RELATED ART

Conventional examination methods, which use a pressure sensor invasively inserted into a blood vessel, or an ultrasonic Doppler flow sensor or a pressure sensor externally pressed against a blood vessel, have been well known. In case that a bypass surgery for supplying a blood flow into the downstream of a blood vessel by bypassing the occluded portion using a graft (generically indicates implanted biological blood vessels), the blood pressure, the blood flow velocity, and blood flow rate of given sites of a human body are measured and examined to evaluate the effect of the bypass surgery.

For example, FIG. 19 is a view explaining the method for evaluating the prognosis of circulation reconstruction of a patient with lower leg ischemia by the bypass surgery. The lower leg ischemia is caused by an occluded portion in anywhere in a downstream arterial line to a lower leg, and the bypass surgery was performed on the patient to bypass the occluded portion for directing a blood flow into the lower leg using a graft (generically indicates biological blood vessels). The bypassed blood flow passes down through below knee artery 23 in the lower leg 21 to the top side 25 of a foot in FIG. 19. The prognosis of circulation reconstruction over the entire lower leg 21 can be evaluated by pressing an ultrasonic Doppler velocity indicator 29 against the skin of the dorsal artery of foot 27 on the top side of foot 25.

In this case, the segmental blood pressure measurement method, which measures, examines, and compares the blood pressure, the blood velocity, and the blood flow rate of the given sites of a human body, is used and in particular, the Ankle/Brachial Pressure Index (API) method and the Ankle/Brachial Blood Index (ABI, blood instead of pressure) method are well known. The API method measures both of blood pressures at an upper arm and a lower leg, for example an ankle and the ratio between two blood pressures is assumed to be an API, based on which the severity of a vascular disease is diagnosed. Similarly, in the case of the ABI method, the ratio between two blood flow rates is assumed to be an ABI. For example, a manchette is wound around the upper arm and then the ankle and pressurized followed by depressurization to measure the blood flow rates when the first beat is caught, based on which an ABI value is found. The blood flow rate on the top side of foot is found by pressing a velocity indicator 29 against the dorsal artery of foot 27 on the top side of foot 25 to measure the blood velocity and assuming the vessel diameter. The blood flow rate on the upper arm can be found in the same manner as that of the top side of foot.

FIG. 20 is a view explaining the method for evaluating the prognosis of circulation reconstruction through a graft implanted in a patient with a disease in the coronary artery, which supply nutrients into the heart, by the bypass surgery. The coronary artery branches from the ascending aorta 33 in the heart 31 into right coronary artery (generally, simply referred to as RCA) 35, left anterior descending branch (simply referred to as LAD) 37, the first and second diagonal (simply referred to as D), and left circumflex (simply referred to as CIRC) 41. In the figure, the left anterior descending branch 37 has been bypassed using a graft 43. In this case, the sensor unit of the Doppler velocity indicator 45 has been clipped on the circumference of the graft 43 to evaluate the parameters such as the maximum value for the blood flow rate of blood passing through the graft 43 during the surgery. It should be noted here that in the case of coronary-artery bypass surgery, the blood flow rate can be directly evaluated without assumption of the vessel diameter of the graft 43, by clipping the sensor unit around the circumference of the graft 43, while since the opened chest is closed after the surgery has been finished, the prognosis of circulation reconstruction can not be evaluated.

In addition, besides the above mentioned evaluation of ABI values and the maximum values for coronary-artery bypass vessel flow amounts, the measurement methods, in which for example arterial blood flow velocity waveforms are represented in the form of frequency analysis or zero crossing, have been known.

Vascular diseases and bypass vessels can be evaluated and examined using the segmental measurement method, in particular by evaluating ABI values of the patient with lower leg ischemia above mentioned and the maximum values for blood flow rates passing through the bypass vessel in a cardiac coronary artery. In the segmental blood pressure measurement method for finding ABI values and others, it is necessary to measure the blood flow rates at more than one given site.

In addition, during and immediately after the surgery, the patient is in rest state and the blood flow velocity and the blood flow rate values of the patient are measured under the condition of the resting blood pressure. Ten days after the surgery, the prognosis of circulation reconstruction of the patient is evaluated under the blood pressure condition in the normal daily life. Accordingly, in clinical cases, for example the ABI value does not always keep pace with the prognosis of vessel reconstruction of the patient after the bypass surgery. Similarly, the maximum value of blood flow rate of blood flow passing through the coronary bypass vessel does not always keep pace with the prognosis of vessel reconstruction.

In addition, expertise and experience are essential to diagnose diseases based on the displayed frequency analysis or zero crossing data on arterial blood flow velocity waveforms.

The present invention is intended to solve these problems and the object of the present invention is to provide a vascular disease examination system and a bypass vascular examination system capable of performing an accurate and recognizable examination by finding the feature quantities of the blood velocity waveform or the blood pressure waveform or the blood flow rate and of comparing the results of the examination with the prognosis of circulation reconstruction.

DISCLOSURE OF THE INVENTION

The vascular disease examining system of the present invention intended to solve the problem above mentioned is characterized in that it has a waveform analysis unit for obtaining the feature quantities of the waveform based on at least one of the blood flow velocity waveform signals and the blood pressure waveform signals output from the measurement system, which measures at least one of the blood flow velocity and the blood pressure and an output unit for outputting the waveform feature quantities found in the waveform analysis unit.

In addition, the bypass vascular diagnosing system of the present invention is characterized in that it has waveform analysis unit for obtaining the feature quantities of at least one of the blood flow velocity waveform signals and the blood pressure waveform signals and the blood flow rate waveform signals output from the measurement system, which measures one of the blood flow velocity and the blood pressure and the blood flow rate and an output unit for outputting the waveform feature quantities found in the waveform analysis unit. Moreover, with respect to the vascular disease examination system or the bypass vascular diagnosing system, the waveform feature quantities are preferably time constants.

Furthermore, with respect of the vascular disease examination system or the bypass vascular diagnosing system of the present invention, the waveform feature quantities are preferably Fourier transform values or differentiated values or integrated values.

Additionally, with respect to the vascular disease examination system or the bypass vascular diagnosing system of the present invention, the waveform feature quantities are preferably the rising/falling times of the waveform of at least one of the blood flow velocity and the blood pressure and the blood flow rate.

Moreover, with respect to the vascular disease examination system or the bypass vascular diagnosing system of the present invention, the waveform feature quantities are preferably the sharpness of the waveform.

Furthermore, with respect to the vascular disease examination system or the bypass vascular diagnosing system of the present invention, the waveform feature quantities are preferably the slope of a line connecting two points, the lowest and highest values in one cycle of at least one of the blood velocity waveform and the blood pressure waveform and the blood flow rate.

Furthermore, with respect to the vascular disease examination system of the present invention, the waveform analysis unit preferably finds an equivalent resistance value and an equivalent compliance value based on at least one of the blood flow velocity waveform signal and the blood pressure waveform signal, respectively.

Additionally, with respect to the bypass vascular diagnosing system of the present invention, the waveform analysis unit preferably finds the equivalent resistance value and the equivalent compliance value of a bypass blood vessel based on at least one of the blood pressure waveform signal and the blood flow rate waveform signal, respectively.

Moreover, the vascular disease examination system of the present invention is characterized in that it has an equivalent constant calculation means for calculating the equivalent constant for the blood vessel for establishing the relationship between the blood flow velocity and blood pressure based on the waveform signals output from a measurement system, which measures the blood flow velocity and the blood pressure and a dynamic bypass vascular condition calculation means for calculating the blood flow velocity values under the virtual blood pressure condition, in which a load is exerted on the blood vessel, using the equivalent constant to find the dynamic blood vessel condition.

Furthermore, the bypass vascular examining system of the present invention is characterized in that it has an equivalent constant calculation means for calculating the equivalent constant for the bypass blood vessel for establishing the relationship between the blood flow rate and blood pressure based on their waveform signals output from the measurement system, which measures the blood flow rate and the blood pressure and a dynamic bypass vascular condition calculation system for calculating the blood flow rate under the virtual blood condition, in which a load is exerted on the bypass blood vessel to find the dynamic bypass vascular condition.

The vascular disease examination system of the present invention extracts and outputs the feature quantities of the blood flow velocity waveform of the blood pressure waveform when the measured signals of the blood flow velocity or the blood pressure are input. It enables a physician to examine and diagnose vascular diseases based on the output waveform feature quantities.

By the analysis of an arterial blood flow velocity waveform, it is possible to evaluate the peripheral resistance and blood vessel compliance, being useful in diagnosing nosovascular diseases.

The waveform feature quantity may be in the form of a time constant, a Fourier transform value, a differentiated value, integrated value, rising/falling times, or waveform sharpness.

Any difference in blood flow velocity waveform or blood pressure waveform exists between a normal subject (control) and a patient subject. For this reason, the vascular diseases can be examined and diagnosed based on the waveform feature quantities.

Additionally, the waveform analysis unit is capable of performing more definitive diagnoses based on the blood vessel resistance and compliance values by finding them from the blood flow velocity waveform signal and the blood pressure waveform signal, respectively.

This specification includes the content described in the specification and drawings contained in JP-B No. 188032/2001 and JP-B No. 262965/2001, on which the priority of the present application is based.

BEST MODE FOR CARRYING OUT THE INVENTION

Referencing to accompanying drawings, preferred embodiments of the present invention are described in detail.

Figure 1:
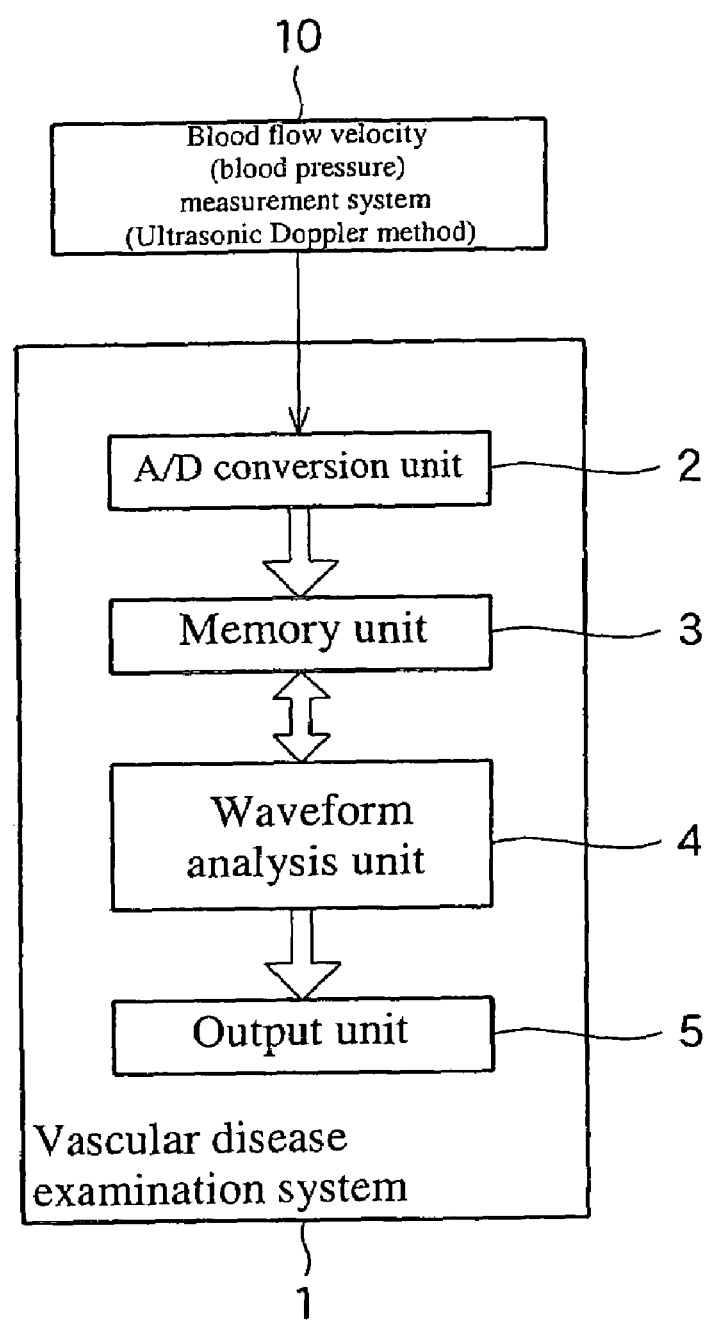
FIG. 1 is a view showing the block configuration of a vascular disease examination system of the present invention.

FIG. 1 is the block configuration diagram of a vascular disease examination system of the present invention. The vascular disease examination system 1 has an A/D conversion unit 2, a memory unit 3, a waveform analysis unit 4, and an output unit 5. Symbol 10 indicates an ultrasonic Doppler blood flow velocity measurement system (or blood pressure measurement system). The blood flow velocity signals (or the blood pressure signals) of the target sites measured by the blood flow velocity measurement system (or the blood pressure measurement system) 10 are supplied into a vascular disease examination system 1.

The A/D conversion unit 2 converts the blood flow velocity (or blood pressure) waveform signals into digital waveform signals. The digital waveform signals are corresponded with time-series data and stored in a memory unit 3. A waveform analysis unit 4 finds waveform feature quantities based on the digital waveform signals stored in the memory unit 3. This waveform analysis unit 4 is composed of a central processing unit (CPU) or a digital signal processor (DSP) and a waveform analysis program. An output unit 5 outputs the waveform feature quantities found at the waveform analysis unit 4. This output unit 5 is composed of an image display system, for example a monitoring device. Note that a printer for printing out the waveform feature quantity output from the output unit 5 may be incorporated in the output unit 5.

Almost similarly, in the block diagram of the bypass vascular examining system according to another embodiment of the present invention, a blood flow rate measurement system (or blood pressure measurement system) may be used instead of the blood flow velocity measurement system 10 shown in FIG. 1, and the blood flow rate signals (or blood pressure signals) measured at the target sites are supplied to the bypass vascular disease examination system instead of the vascular disease examination system.

Figure 2:
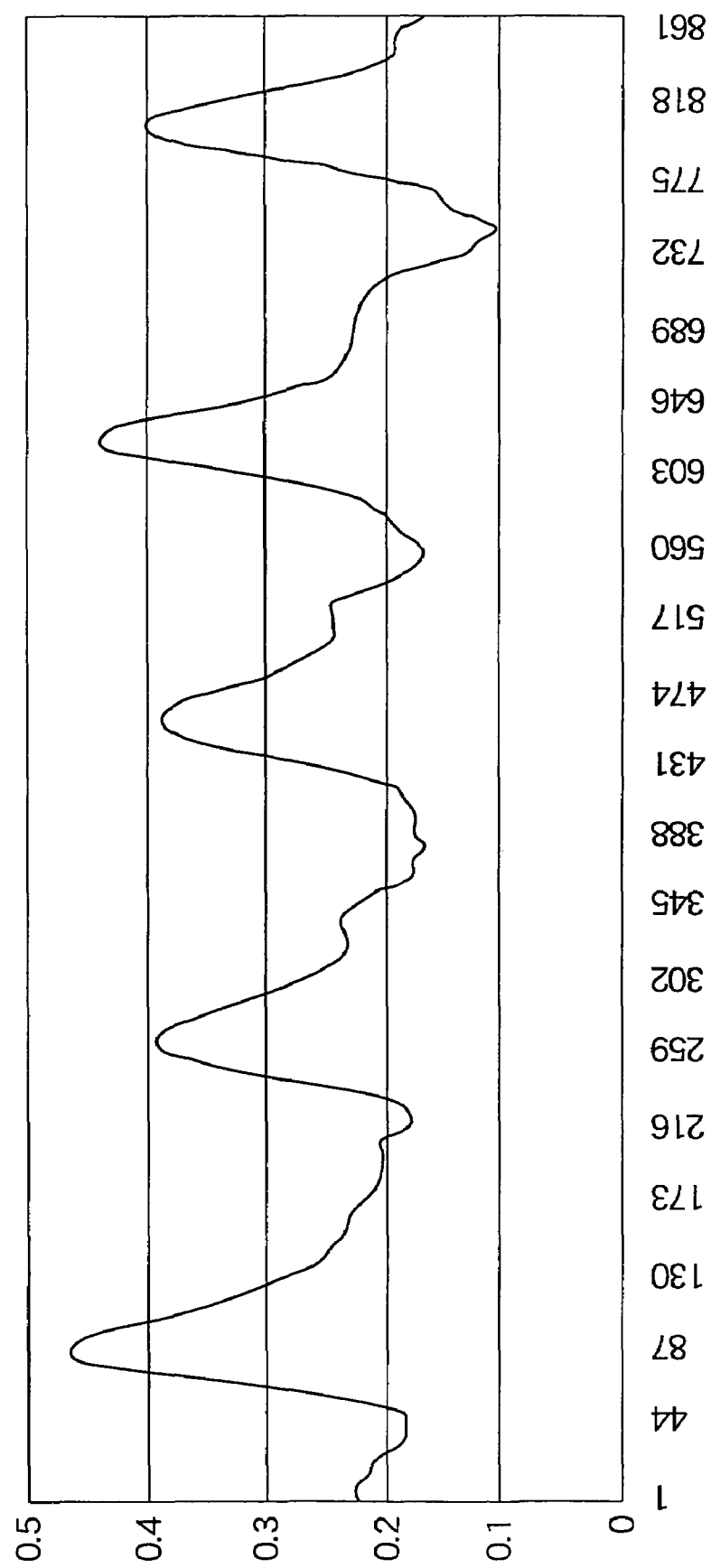
FIG. 2 is a graph showing the blood flow velocity waveform measured on a patient with an arterial disease prior to the surgery.
Figure 3:
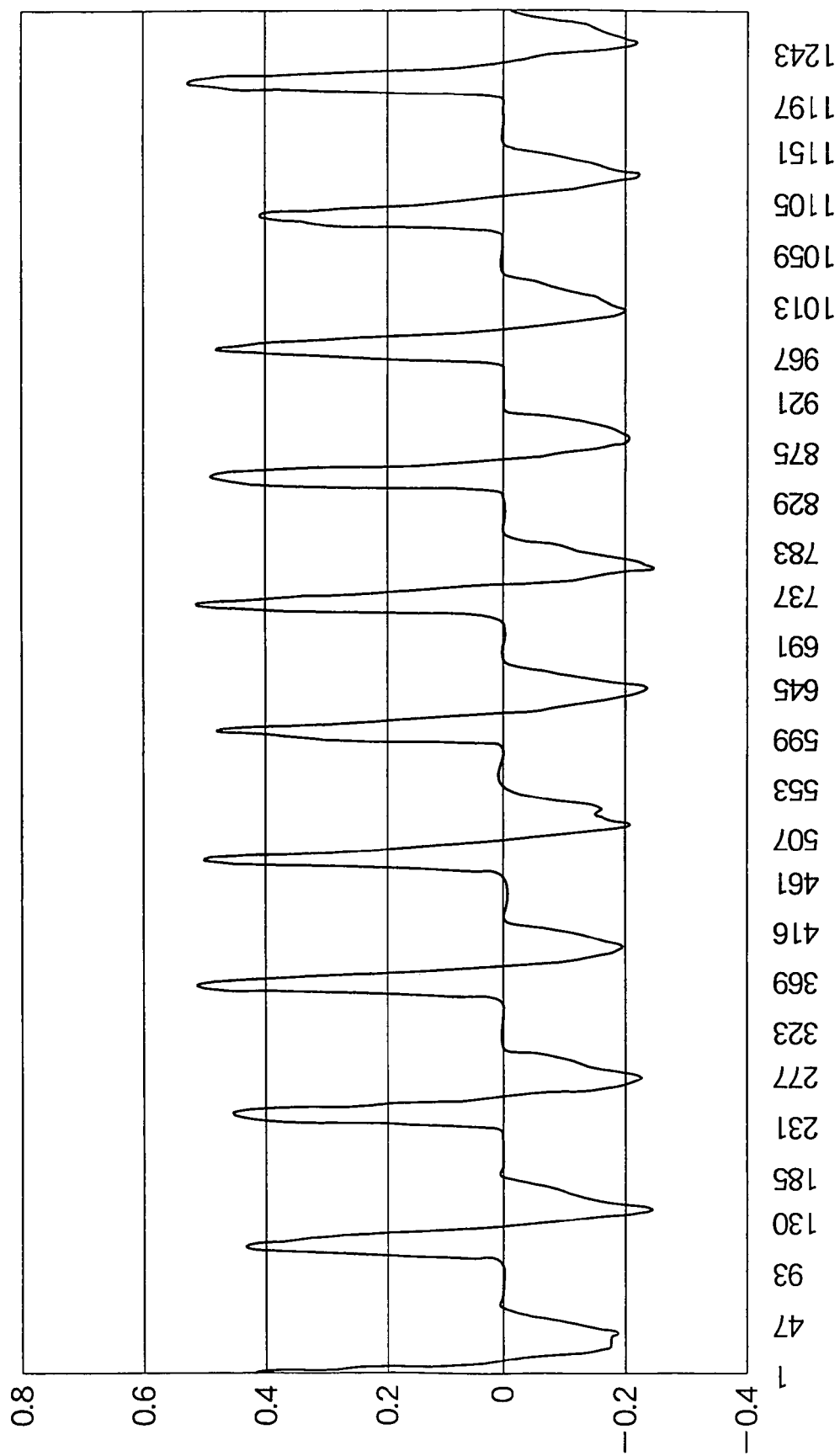
FIG. 3 is a graph showing the blood flow velocity waveform measured on the patient immediately after the surgery.
Figure 4:
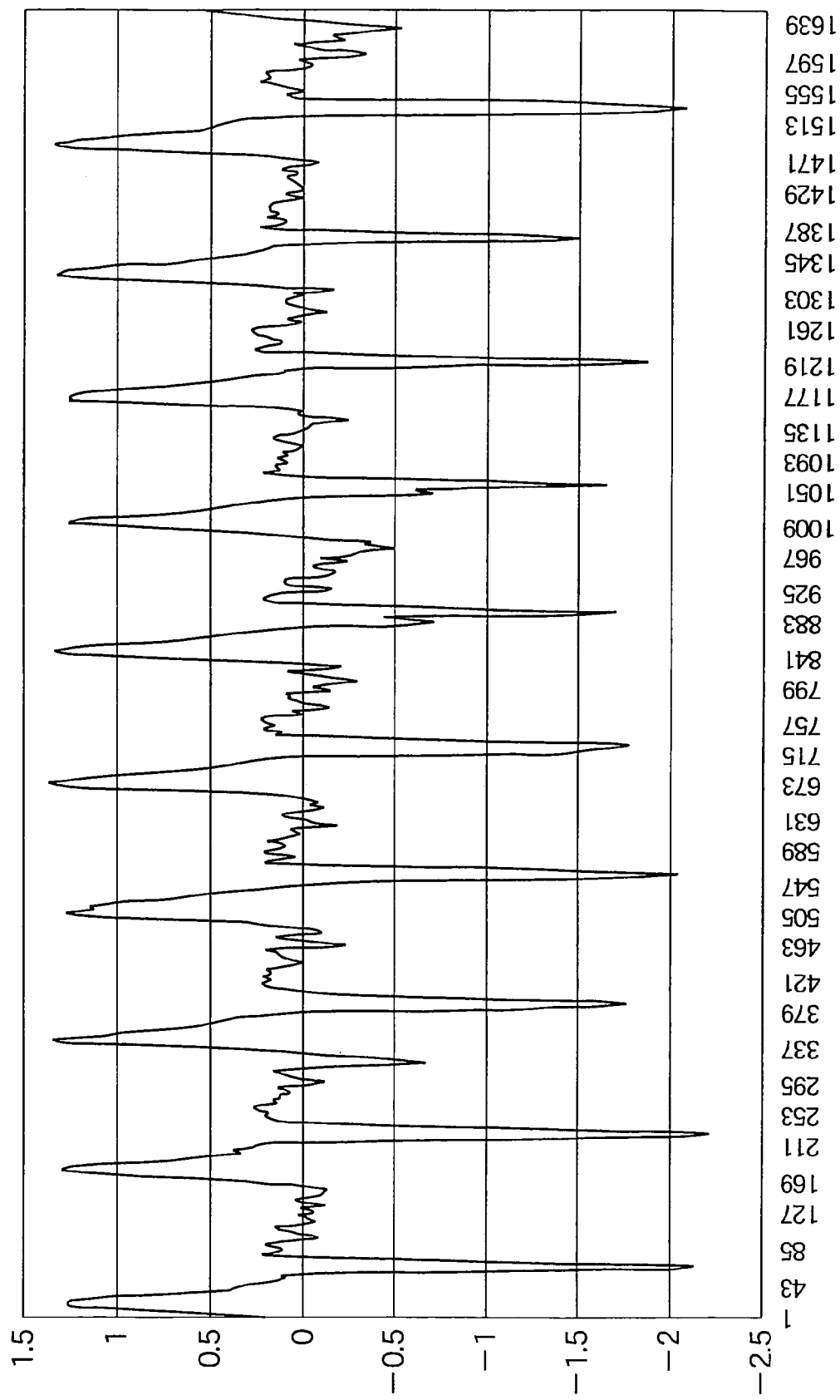
FIG. 4 is a graph showing the blood flow velocity measured on the patient one week after the surgery.

FIGS. 2 to 4 are views showing the results of the evaluation of the prognosis of circulation reconstruction by performing the bypass surgery on the occluded artery of a patient with lower leg ischemia and pressing a Doppler blood flow velocity indicator against the dorsal artery of foot to obtain blood flow velocity signals. FIG. 2 is a graph showing the blood flow velocity waveform measured on the patient with arterial disease prior to the surgery, FIG. 3 is a graph showing the blood flow velocity waveform measured on the patient immediately after the surgery, and FIG. 4 is a graph showing the blood flow velocity waveform measured on the patient one week after the surgery. In these graphs, a vertical axis indicates blood flow velocity data and a horizontal axis indicates time data. Note that the values along the horizontal axis are indicated by corresponding sampling numbers used in sampling blood flow velocity signals at a given sampling period.

As known from these graphs, in the case of a patient with advanced arterial occlusion prior to the bypass surgery, the rising-falling slope of the blood flow velocity waveform is moderate, while it is sharp after the surgery.

Figure 5:
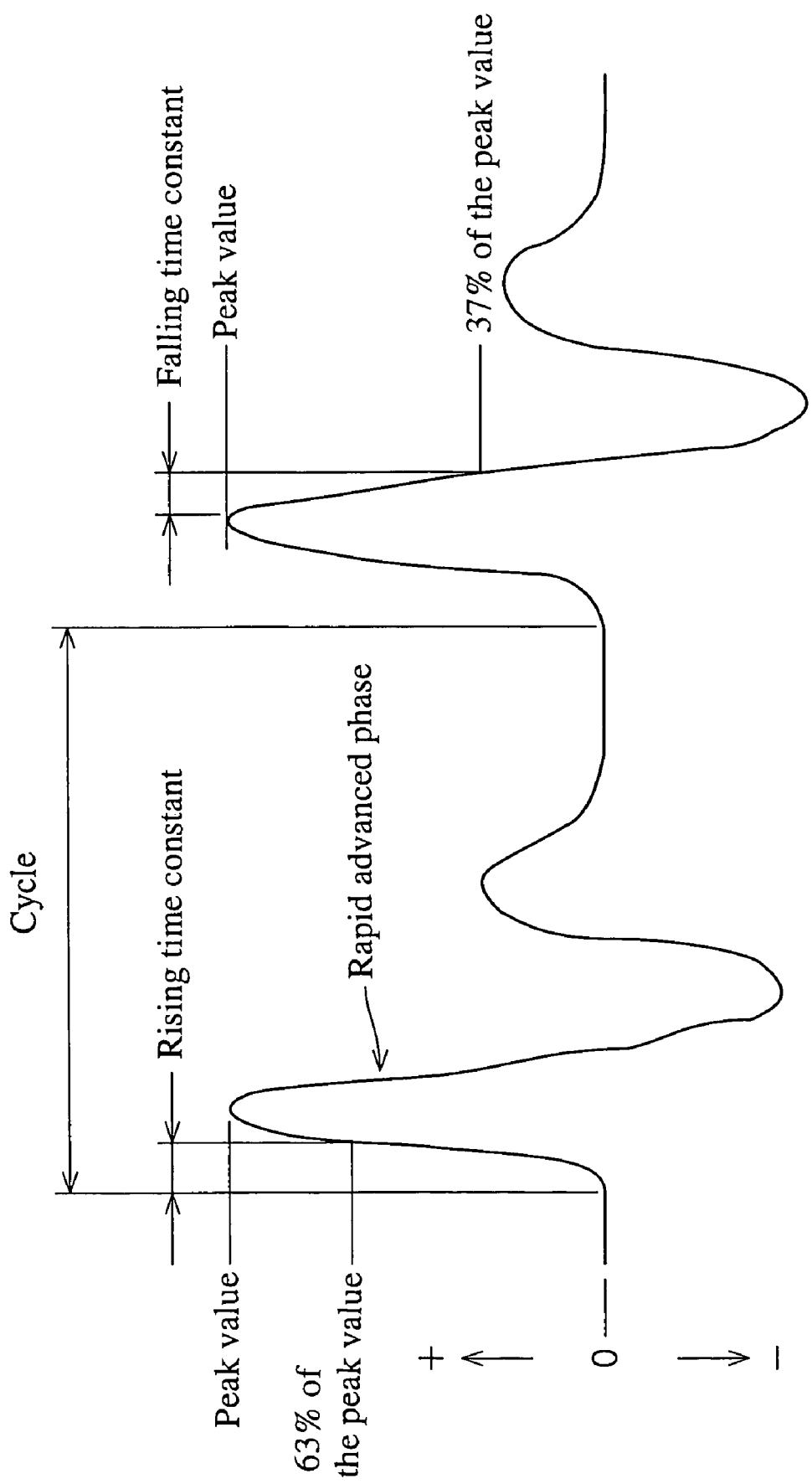
FIG. 5 is a view explaining one preferred embodiment of the present invention, in which a time constant is found as a waveform feature quantity.

FIG. 5 is a view showing the example of a feature quantity extracted at the waveform analysis unit 5. In FIG. 5, a time constant is found as a waveform feature quantity. The waveform analysis 4 recognizes one-peak rapid advanced phases based on, for example the normal values on the normal side to cut out individual periods of a waveform relative to their corresponding rapid advanced phases. The waveform analysis unit 4 finds the time required for the blood flow velocity value to rise from 0 up to about 63% of the peak value to be used as a rising time constant. The waveform analysis unit 4 finds the time required for the blood flow velocity value to drop from the peak value down to about 37% of the peak value to be used as a falling time constant. The waveform analysis 4 finds the riding time and falling time constants for each period, obtains an average for each of the periods, and outputs the rising and falling time constants. Note that the waveform analysis 4 may find only the rising time constant for outputting.

On the screen of the image display device, which is a component of the output unit 5, not only the blood flow velocity waveform but also the rising and falling time constants are displayed. Based on these data, physicians and others can determine the severity of the vascular disease. The time constant values obtained from the patients with vascular diseases such as angiostenosis and blood vessel occlusion tend to have large values.

Note that the thresholds for determining whether a patient is normal and for determining the severity of the vascular disease must have been established so that the waveform analysis unit 4 may compare the calculated time constants with the associated thresholds for determining the severity of the vascular disease to output the results of the determination.

Alternatively, a Fourier transform value, a differentiated value, or an integrated value may be used as a waveform feature quantity.

Figure 6:
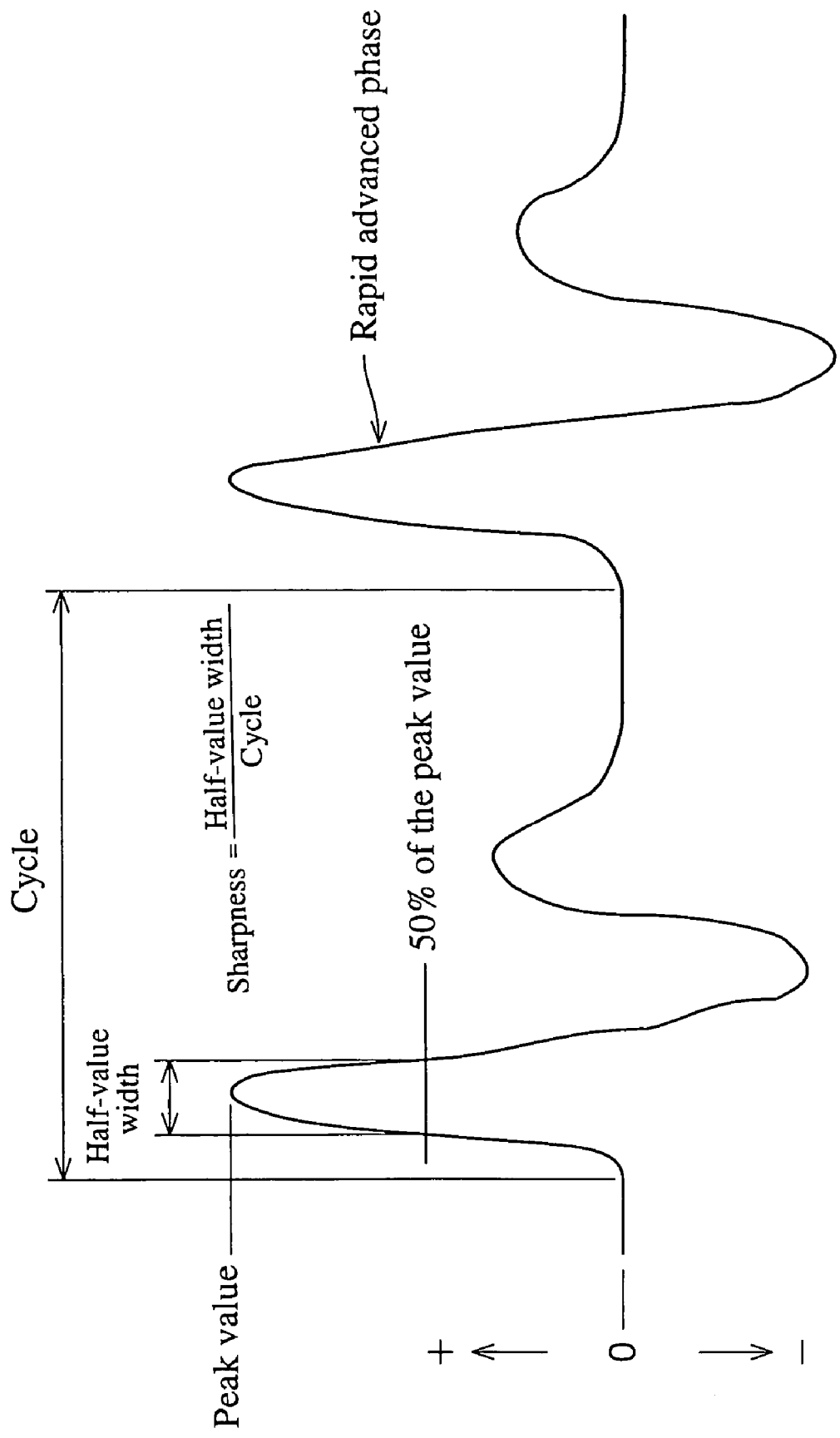
FIG. 6 is a view explaining another preferred embodiment of the present invention, in which sharpness is found as a waveform feature quantity.

Besides, sharpness may be used as a waveform feature quantity. FIG. 6 is a view showing the example of sharpness obtained as a waveform feature quantity. The period up to the 50% point of the peak value for the rapid advanced phase is found and the obtained value is assumed to be a half-value width. The ratio of the period of the half-value width to the period of one cycle (half-value width/cycle) is found and the obtained value is assumed to be sharpness.

Note that although in the preferred embodiments of the present invention, the feature quantity of the blood flow velocity waveform is obtained as an example, but the feature quantity of the blood pressure waveform or the blood flow rate data may be obtained.

Figure 7:
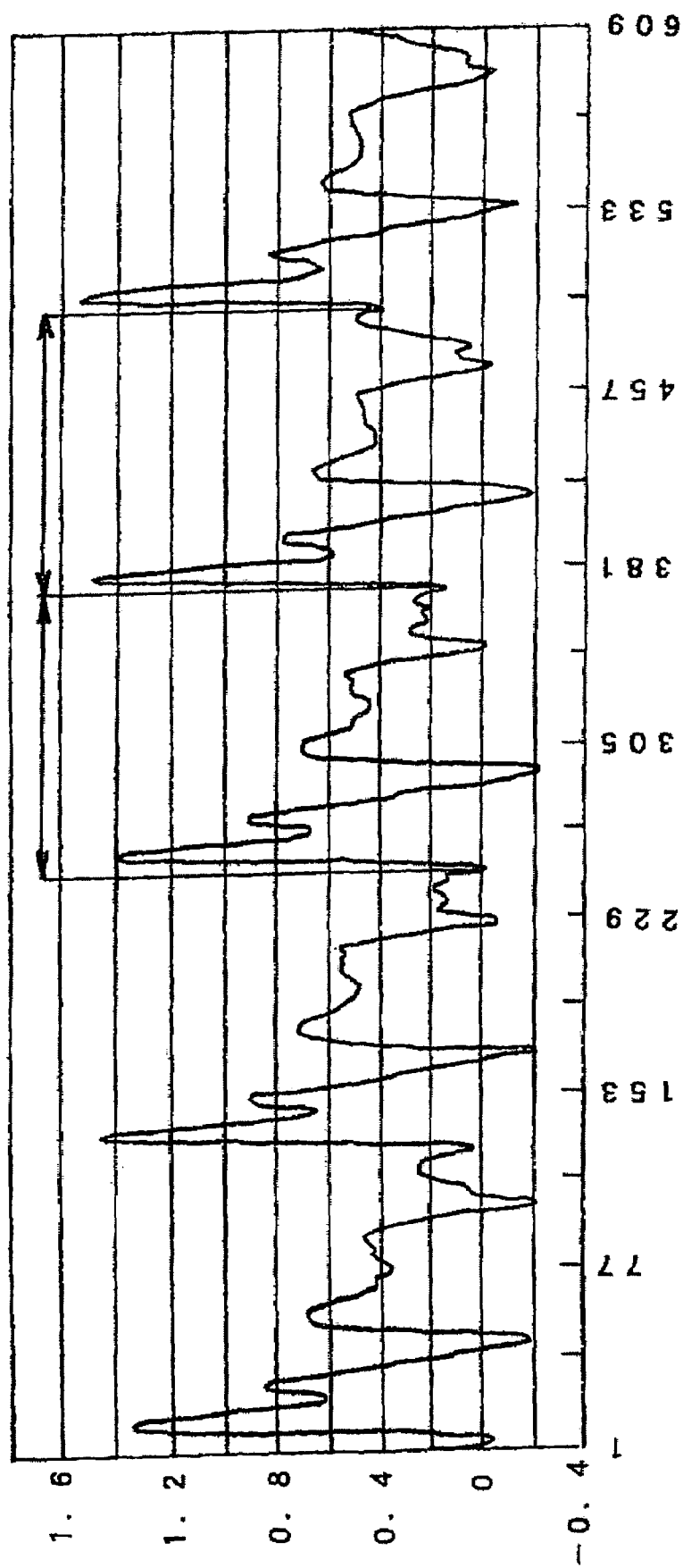
FIG. 7 is a view showing the example of a blood flow rate waveform of a blood flow passing through the typical bypass blood vessel implanted in cardiac coronary artery.

In FIG. 7 showing the example of the blood flow rate waveform of blood flow passing through the typical cardiac coronary arterial bypass, the blood flow rate is measured by bypassing the occluded arterial portion into LAD using internal thoracic artery as a graft and clipping the sensor unit of the Doppler blood flow rate indicator on the bypass blood vessel. The values along the horizontal axis indicate the time data and the values along the vertical axis indicate blood flow rate data. Note that the values along the horizontal axis are indicated by the sampling number used in sampling.

The blood flow rate waveform of blood flow passing through the cardiac arterial bypass blood vessel shown in FIG. 7 has two peaks in the rapid advanced phase within one heartbeat rhythm unlike those for the dorsal artery of foot shown in FIGS. 2 to 4. This is caused by two heart stroke periods, diastole, and systole. This means that blood is supplied into general peripheral artery in the diastole period, while blood is easy to flow into cardiac coronary artery because the cardiac muscle is relaxed even in the systole period, forming two peaks in the rapid advanced phase corresponding to these periods.

Figure 8:
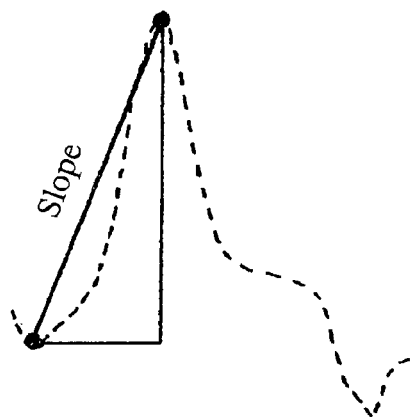
FIG. 8 is a view explaining further another preferred embodiment of the present invention, in which when the slope at waveform rising is used as a blood velocity waveform feature quantity, the slope is defined.

FIG. 8 is a view showing the slope defined using the slope at a waveform starting point as a feature quantity of blood flow velocity waveform obtained from the patient with lower leg ischemia. The lowest and highest points of the blood flow velocity are connected by a line and the obtained slope is assumed to be a feature quantity. This slope represented by means of a blood flow velocity/time is converted into the voltage/voltage waveform data at the blood flow velocity measurement system 10 and the waveform data is output directly to the output unit 5 to be in the form of the length along the Y axis/length along the X axis. The normalization of these transformation gives the length along the Y axis and the length along the X axis of the graphic shown in FIG. 8 for comparison.

FIGS. 9A and 9B and FIGS. 11A and 11B are graphs showing the variation in normalized slope prior to, immediately after, and given days after the bypass surgery. In this case, the obtained data was compared with the ABI values.

Figure 9A:
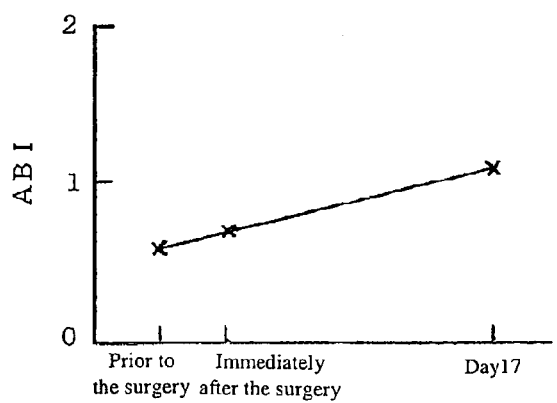
FIGS. 9A and 9B are graphs showing the ABI values measured by the prior art system prior to, immediately after, and given days after the bypass surgery, and the result of the variation in normalized slope in one case obtained in the preferred embodiment of the present invention.
Figure 9B:
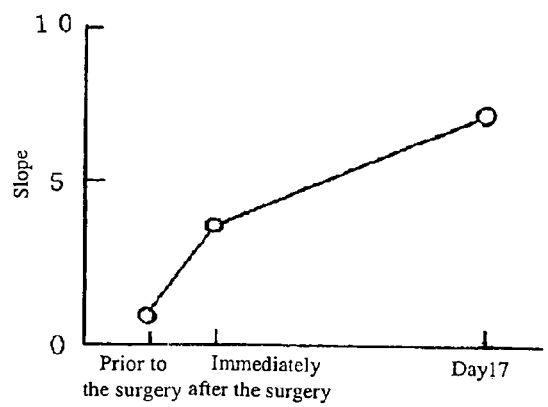

For example, FIG. 9A shows variations in ABI value prior to, immediately after, and 17 days after the bypass surgery. Meanwhile, FIG. 9B shows variations in normalized slope. In the case of this patient, the API value was slightly improved by the bypass surgery and 17 days after the surgery, the ABI value increased. The normalized slope was significantly improved by the bypass surgery, especially at the point of 17 days after the surgery.

Figure 10A:
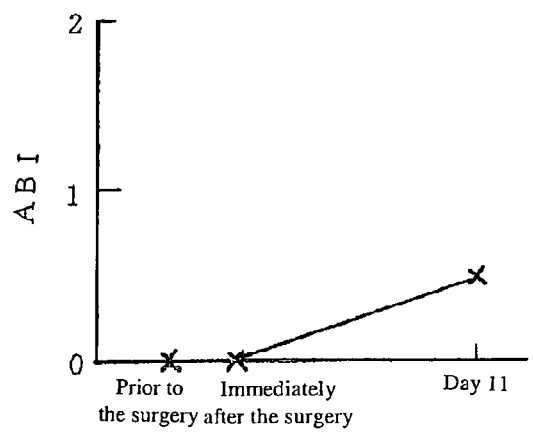
FIGS. 10A and 10B are graphs showing the ABI values measured prior to, immediately after, and given days after the bypass surgery, by the prior art system and the result of the variation in normalized slope in another case obtained in the preferred embodiment of the present invention.
Figure 10B:
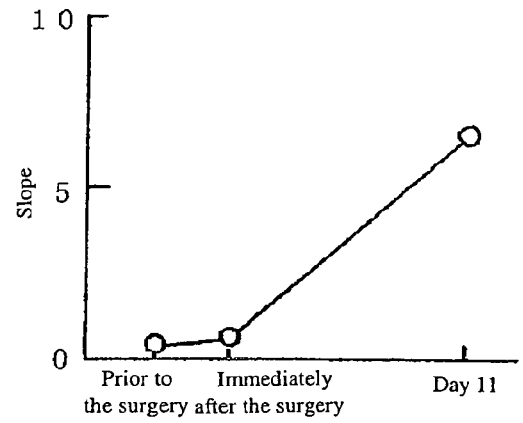

In the cases of the patients in FIGS. 10A and 10B, the ABI value was 0 prior to the bypass surgery and did not recovered even after the surgery. On the other hand, the normalized slope was improved by the bypass surgery, and 11 days after surgery, the ABI value was recovered and the normalized slope was significantly improved.

Figure 11A:
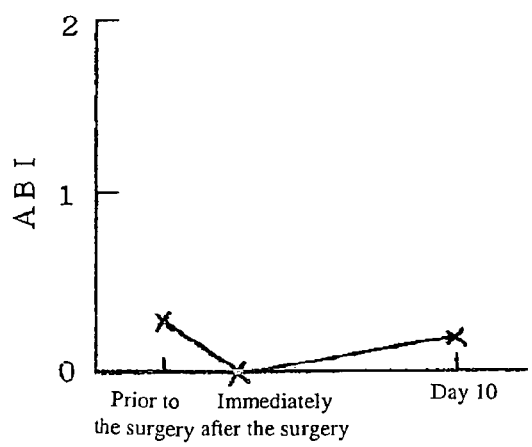
FIGS. 11A and 11B are graphs showing the ABI values measured prior to, immediately after, and given days after the bypass surgery, by the prior art system and the result of the variation in normalized slope in further another case obtained in the preferred embodiment of the present invention.
Figure 11B:
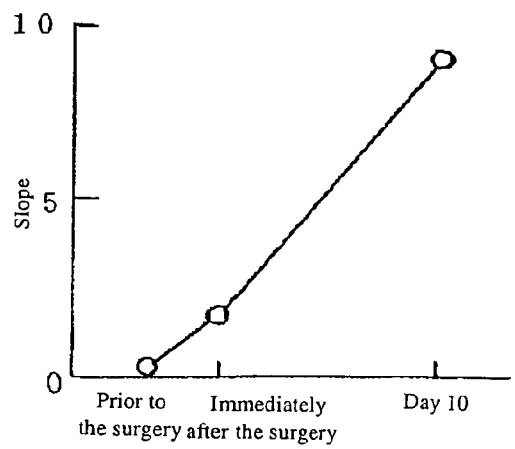

In the cases of the patients in FIGS. 11A and 11B, the ABI value dropped down to 0 but the normalized slope was significantly recovered by the bypass surgery and 10 days after the surgery, the ABI value was slightly recovered but not to its original value prior to the surgery, while the normalized slope was more significantly improved.

Thus, examining variations in ABI value to evaluate whether the value is improved, not improved/decreased, and decreased, no variations in ABI value keep pace with the prognosis of circulation reconstruction, while the normalized slope was outstandingly improved, keeping pace with the prognosis of circulation reconstruction.

For this reason, it is understood that with respect to the bypass surgery performed on the patient with lower leg ischemia, the normalized slope of the blood flow velocity waveform of dorsal artery of foot is useful for evaluating the prognosis of circulation reconstruction after the surgery, that is, it is an effective waveform feature quantity for the blood vessel disease examining system.

Figure 12:
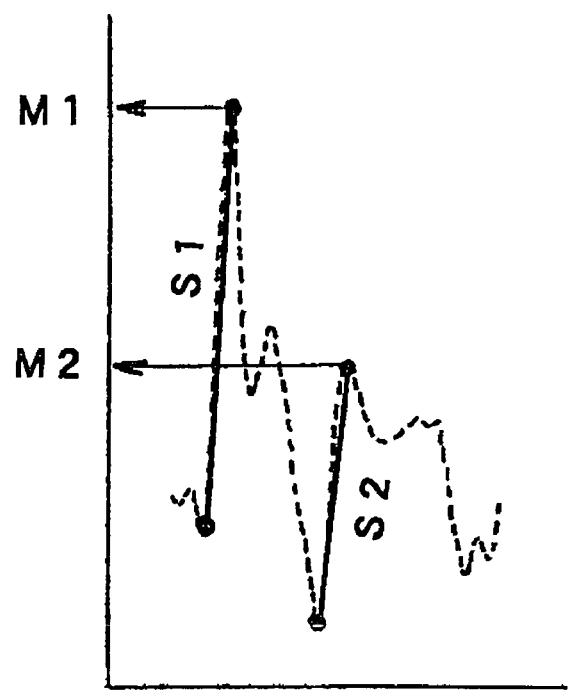
FIG. 12 is a view explaining the preferred embodiment of the present invention, in which the normalized slope is defined for the blood flow rate of a cardiac coronary arterial bypass blood vessel.

FIG. 12 is a view explaining the defined normalized slope for the blood flow rate waveform of the cardiac coronary arterial bypass blood vessel. In this case, since two types of waveforms were obtained corresponding to two periods of one heartbeat rhythm, distal and systole, the slopes normalized to the rising time periods for the distal and systole periods were found and classified into S1 and S2. Similarly, the maximum values for the blood flow rate were classified into M1 and M2 corresponding to the distal and systole periods. In this case, the blood flow rate values were also normalized for comparison.

FIGS. 13A to 16B show the comparison in size between the normalized slopes S1 and S2 and the maximum values M1 and M2 for blood flow rate in the case with three bypass grafts implanted by the cardiac coronary arterial bypass surgery. Three bypass points vary among the individual patients, though three points are generally selected from RCA, LCD, CIRC, and the first and second Ds.

Figure 13A:
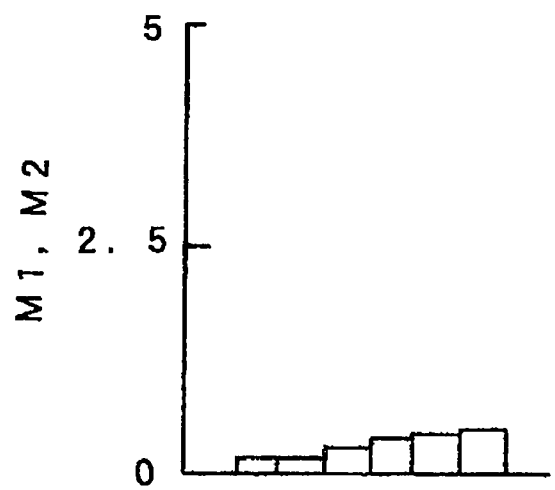
FIGS. 13A and 13B are views showing the comparison between the size of the normalized slope in the preferred embodiment of the present invention and the maximum value for blood flow rate in one case with three bypass grafts implanted by the coronary arterial bypass surgery.
Figure 13B:
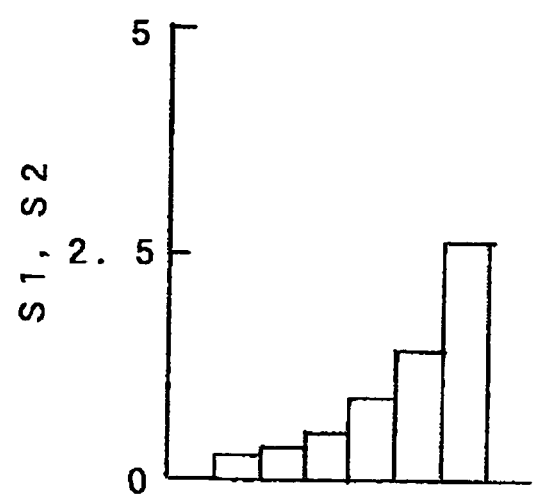
Figure 14A:
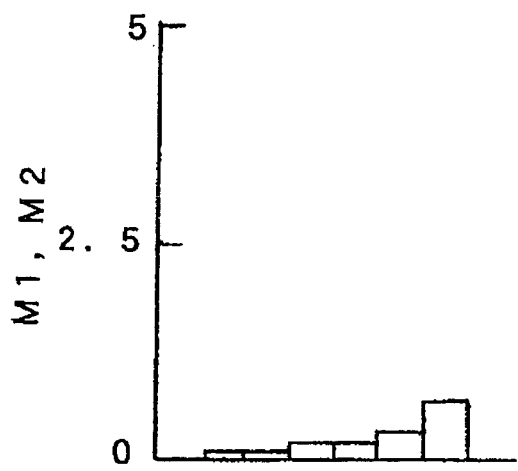
FIGS. 14A and 14B are views showing the comparison between the size of the normalized slope in another preferred embodiment of the present invention and the maximum value for blood flow rate in one case with three bypass grafts implanted by the coronary arterial bypass surgery.
Figure 14B:
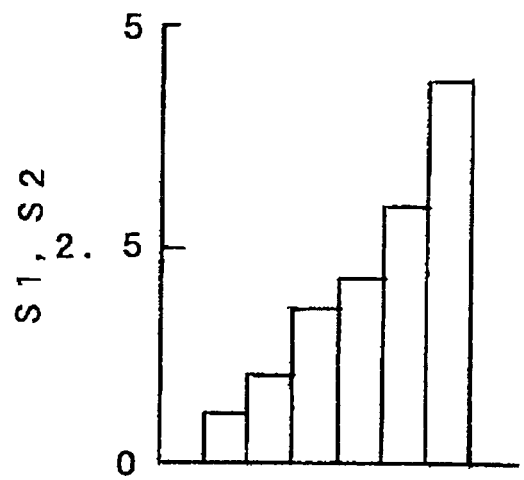
Figure 15A:
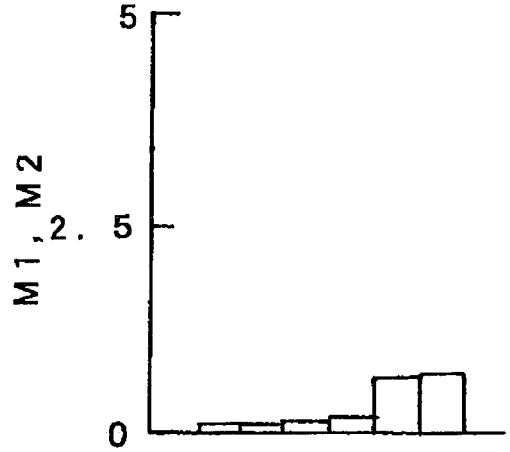
FIGS. 15A and 15B are views showing the comparison between the size of the normalized slope in another preferred embodiment of the present invention and the maximum value for blood flow rate in one case with three bypass grafts implanted by the coronary arterial bypass surgery.
Figure 15B:
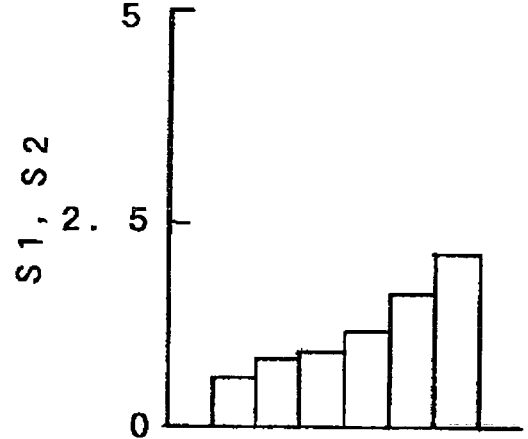
Figure 16A:
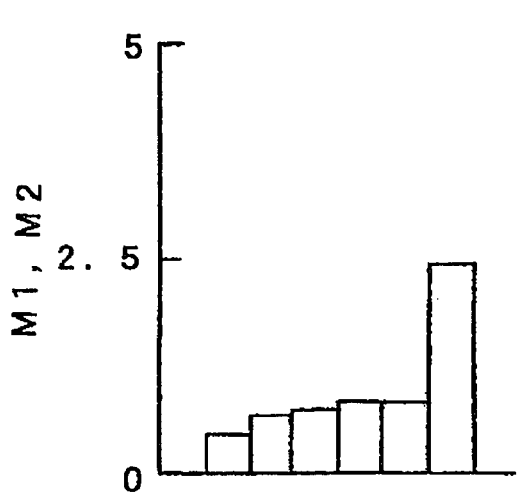
FIGS. 16A and 16B are views showing the comparison between the size of the normalized slope in another preferred embodiment of the present invention and the maximum value for blood flow rate in one case with three bypass grafts implanted by the coronary arterial bypass surgery.
Figure 16B:
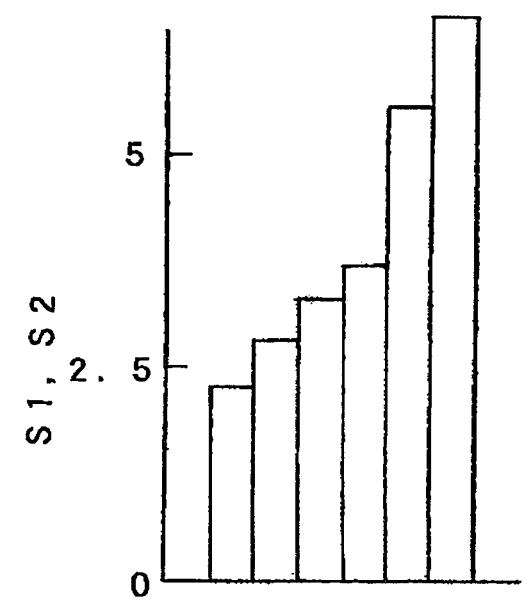

For example, FIG. 13A shows the values for the normalized maximum blood flow rate at three bypass points rearranged in an ascending order of values to find the rang of values. In this case, the minimum value was 0.15 and the maximum value was 0.45. FIG. 13B shows the normalized corresponding slopes rearranged in an ascending order of values to find the range of values. The minimum value was 0.25 and the maximum value was 2.65.

Thus, no significant difference in maximum blood flow rate among three bypass blood vessels, namely focusing on the normalized blood flow rate only, no significant difference was observed in evaluating the prognosis of circulation reconstruction for the bypass blood vessel. It is understood that a significant difference in normalized slope was observed in three bypass blood vessels.

Similarly, it may be applied to the different cases shown in FIGS. 14A, 14B, 15A, 15B, 16A, and 16B. Particularly, in the case of cardiac coronary arterial bypass surgery, since the opened chest is closed after the surgery has been finished, the evaluation of the characteristics of the bypass blood vessels provides a very useful means in using the normalized slope as a feature quantity, which causes the evaluation of significant difference in circulation reconstruction.

Thus, it is understood that in the case of cardiac coronary arterial bypass surgery, the normalized slope of the blood flow rate waveform for the bypass blood vessel is effective feature quantity in evaluating the prognosis of circulation reconstruction by the bypass surgery, namely for the bypass vascular examining system.

Figure 17:
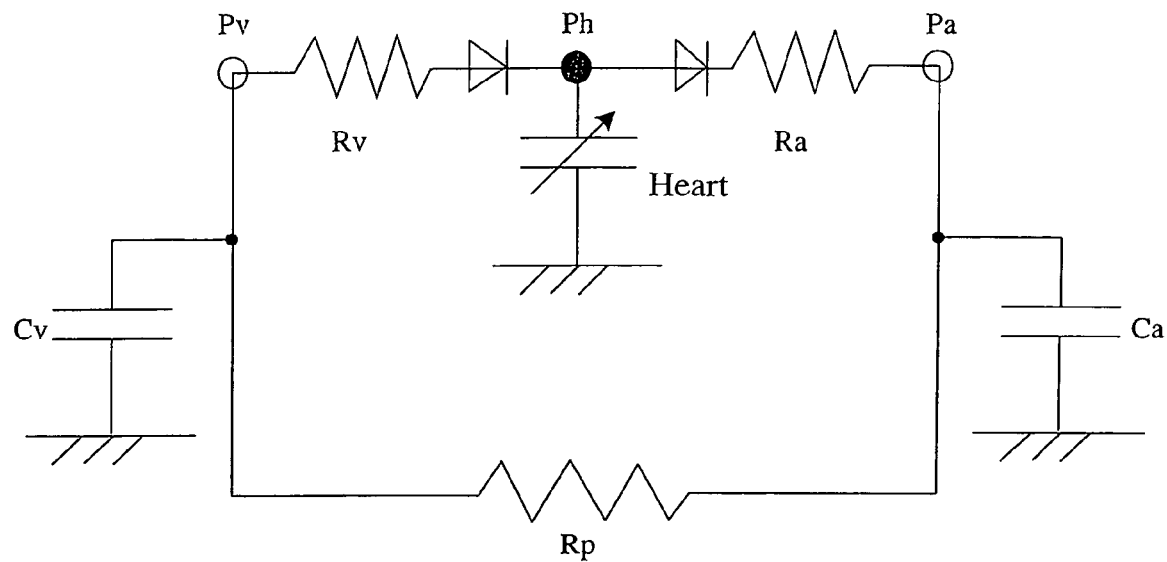
FIG. 17 is a view showing a model of electric circuit equivalent to the systemic circulation system.

FIG. 17 is a view showing a model of electric circuit equivalent to the systemic circulation system. The characteristics of the blood vessel include resistance R for the thinness of the blood vessel (equivalent to the resistance of an electric circuit) and compliance C for the softness of the blood vessel (equivalent to capacitance of the electric circuit). The time constant can be obtained by multiplying C by R and is useful in diagnosing diseases, though resistance R and compliance C are desirably obtained to achieve more definitive diagnosis. Namely, since the time constant discriminates between the thick and hard blood vessel and the thin and soft blood vessel, it is desirable to handle independently two parameters R and C.

The model for the systemic circulation system can be represented as shown in FIG. 17 because a peripheral blood vessel has a large resistance enabling the ignorance of compliance.

Where, Ra is arterial resistance, Ca is arterial compliance, Pa is arterial blood pressure, Rp is peripheral blood vessel resistance, Rv is venous resistance, Cv is venous compliance, Pv is venous blood pressure, and Ph is cardiac blood pressure.

Figure 18:
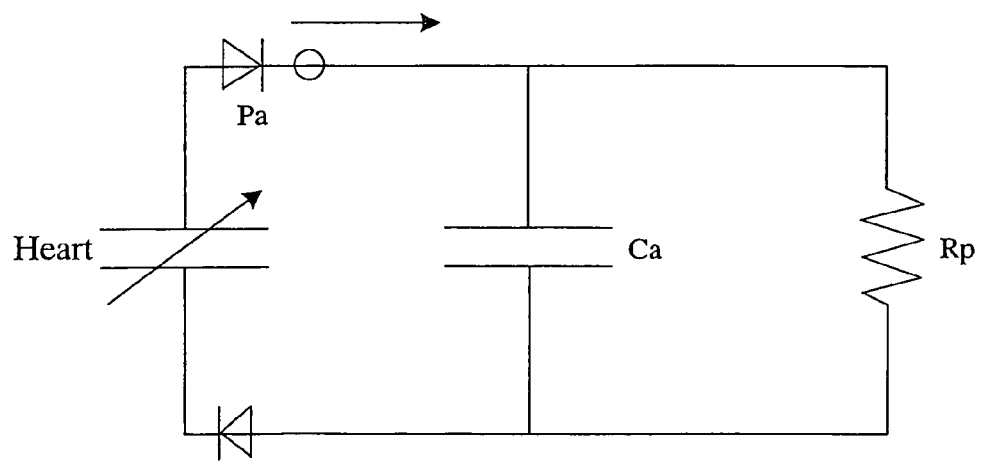
FIG. 18 is a view showing a simple model of electric circuit equivalent to the systemic circulation system.
Figure 19:
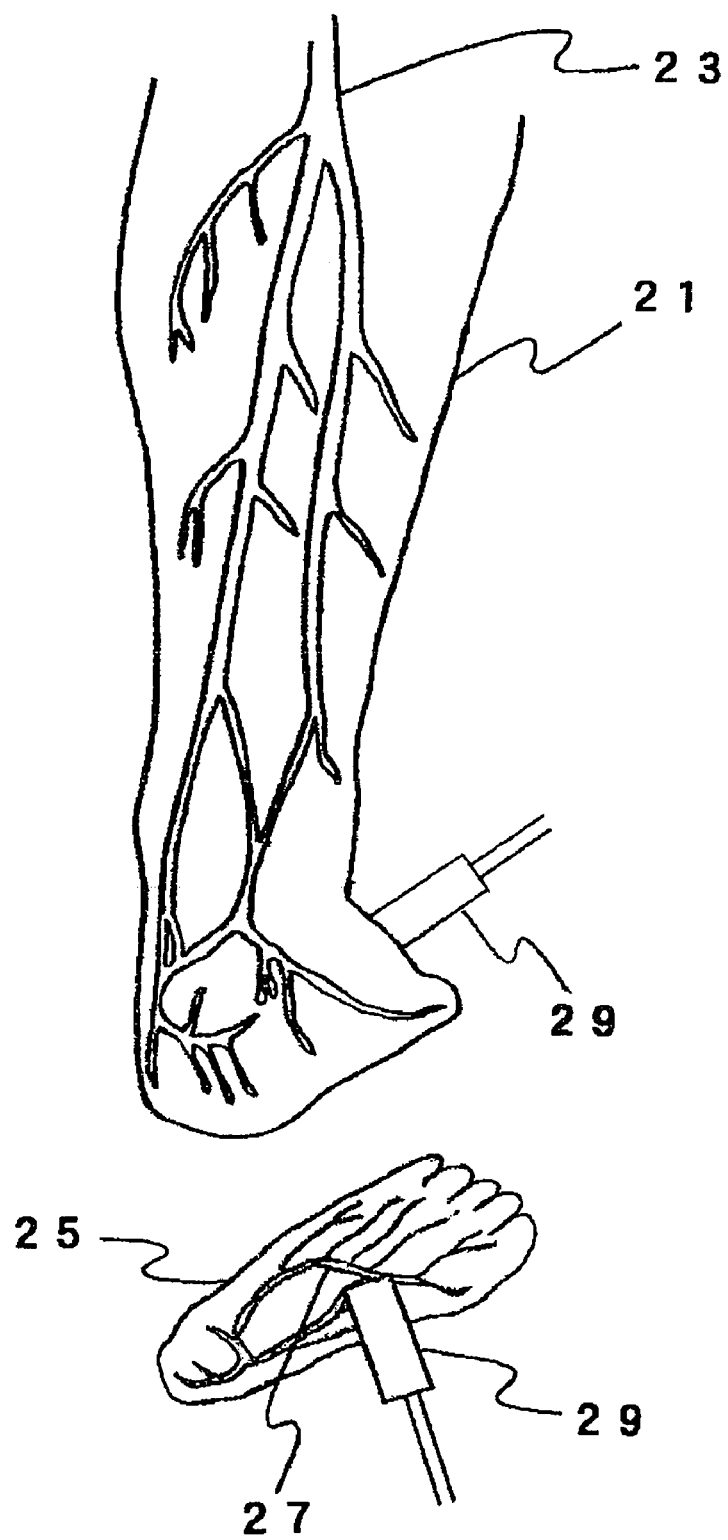
FIG. 19 is a view explaining the prior art method for evaluating circulation reconstruction on the patient with lower leg ischemia by the bypass surgery.
Figure 20:
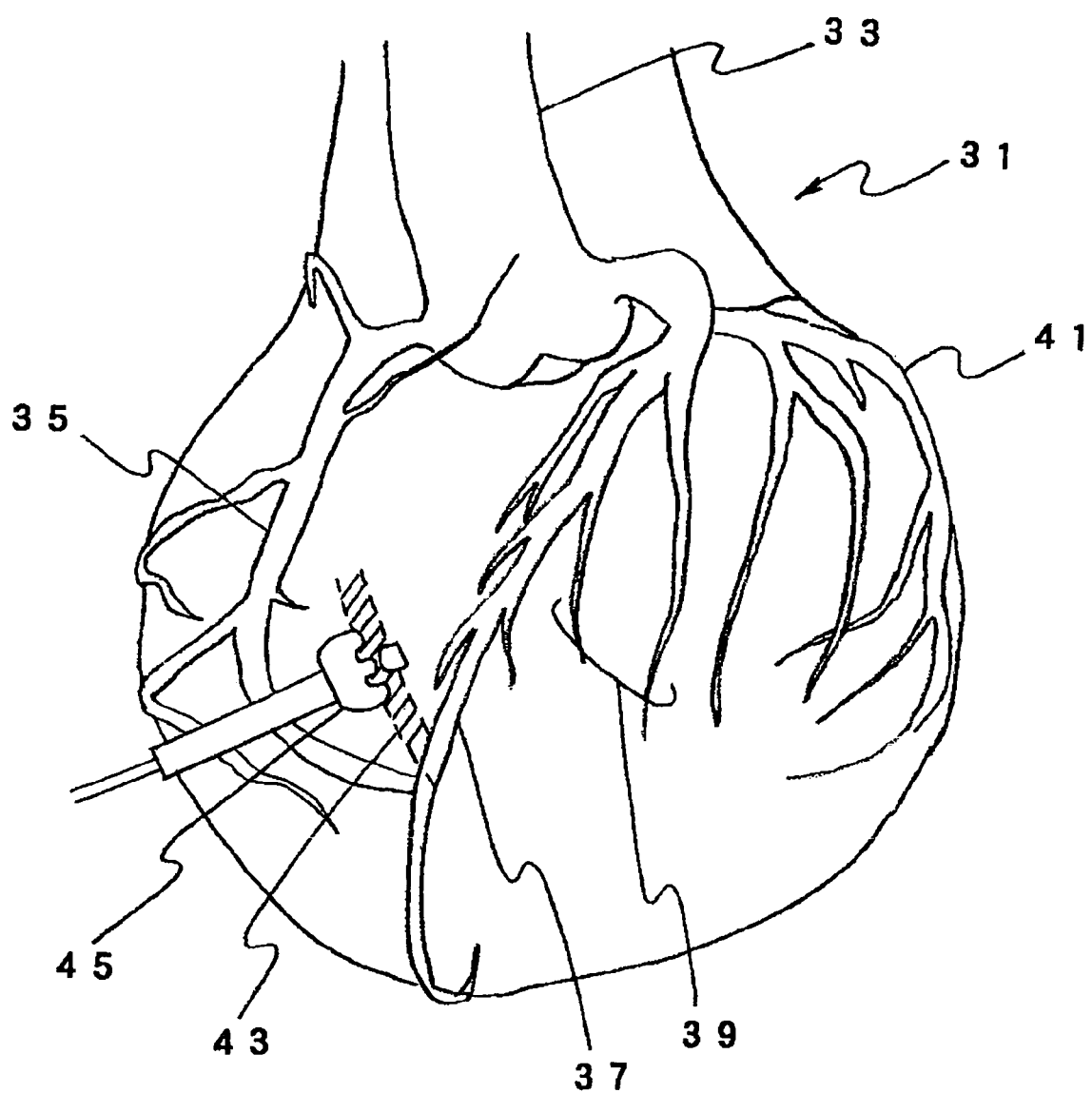
FIG. 20 is a view explaining the prior art method for evaluating circulation reconstruction of blood flow passing through a graft implanted in the patient with a disease in coronary artery supplying nutrients into the heart by the bypass surgery.

FIG. 18 is a view showing the simple model of an electric circuit equivalent to the systemic circulation system. With respect to a vein, since its parameters are almost not changed due to physiological factors and its arterial resistance Ra is smaller than its peripheral blood vessel Rp and can be neglected, the model for the systemic circulation system may be more simplified.

To find resistance R and compliance C, one of these two procedures is followed.

(First method): The blood pressure (equivalent to voltage) and blood flow velocity (electric current) are measured and resistant R and compliance C are identified, individually using any of methods such as the least squares method. In the case of the use of the least squares method, the model formula for the discrete system is established as shown below and using this formula 1 for the model, peripheral blood vessel resistance Rp and arterial compliance Ca can be obtained from many measured blood pressure values V (k) and blood flow velocity values I (k).

Formula (1):

$$V(k+1) = \left(1 - \frac{Ts}{CaRp}\right)V(k) + \frac{Ts}{Ca}\left(1 - \frac{Ts}{2CaRp}\right)I(k)$$

V(k): BP, HR CaRp: Time constant (slope)
Ts: Sampling time Ca: Compliance
I(k): Blood flow velocity or blood flow rate (Second method): A shown in FIGS. 2A to 2B, since a relatively stable period(s) exists in a waveform cycle and in this period, compliance C may be ignored, resistance R is obtained by measuring the blood pressure and blood flow velocity values in this period, the time constants above mentioned are obtained, and compliance C can be found from these time constants and resistance R.

For this reason, with respect to the first method, the formula 1, in which the model for the systemic circulation system shown in FIGS. 17 and 18 is converted from the continuous system into the discrete (digital) system, is used to adapt them to computer-based calculations. Specifically, using many blood pressure values and blood flow velocity values measured in sampling as discrete data, the resistance and compliance constants equivalent to the blood vessel, which are model parameters, are obtained by the least squares method. With respect to the second method, the resistance and compliance constants equivalent to the blood vessel are obtained by measuring the blood pressure value in the period in which the blood flow velocity is relatively stable as well.

The equivalent constants obtained in this manner, which define the relationship between the blood pressure and blood flow velocity values, are specific to the blood vessel, meaning that they stay unchanged under both of the resting and daily life conditions. By obtaining the constants equivalent to the blood vessel using this feature, the relationship between the blood pressure and blood flow velocity values measured on the patients under the various types of daily life styles.

The vascular disease examination system according to further another embodiment of the present invention, which has the equivalent constant calculation means for obtaining the equivalent constants defining the relationship between the blood pressure and blood flow velocity values from the blood pressure and blood flow velocity values and the dynamic blood vessel condition calculation means for calculating the blood flow velocity value under the virtual blood pressure condition, in which a load is exerted on the blood vessel using the obtained equivalent constants to obtain the dynamic blood vessel condition value, is capable of predicting the dynamic condition of the blood vessel.

Namely, assuming that the blood vessel equivalent constants of Ts, Ca, and Rp are given in the formula 1, by substituting an appropriate blood pressure value V(k), the blood flow velocity i(k) can be calculated under the condition of V(k). During and immediately after the bypass surgery, the patient lays rest in bed and the blood flow velocity values measured under such conditions may differ from those measured under the normal daily life condition given days after the surgery. For this reason, the vascular disease examining system is capable of calculating the blood vessel equivalent constants during surgery on a real time basis and estimating, based on the calculated constants, the blood flow velocity values under the condition of the normal daily life given days after the surgery when the blood pressure values under the virtual normal daily life are substituted in the formula (1).

Similarly, the bypass vascular examining system according to further another embodiment of the present invention, which has the equivalent constant calculation means for obtaining the equivalent constants defining the relationship between the blood pressure and blood flow velocity values from the blood pressure and blood flow velocity values and the dynamic blood vessel condition calculation means for calculating the blood flow velocity value under the virtual blood pressure condition, in which a load is exerted on the blood vessel using the obtained equivalent constants to obtain the dynamic blood vessel codition value, is capable of predicting the dynamic condition of the bypass blood vessel implanted by the bypass surgery, making the accurate examination and diagnosis of vascular diseases possible.

The contents of all the publications, patents, and applications referred in this specification are incorporated by reference.

INDUSTRIAL APPLICABILITY

As known from the descriptions above mentioned, the vascular disease examination system and the bypass vascular examining system of the present invention are capable of finding the feature quantities of a blood flow velocity wave form or a blood pressure waveform or a blood flow rate and outputting them in the form of digital values, making the accurate examination and diagnosis of vascular diseases possible.

The invention claimed is:

1. A vascular disease examination system, comprising:

an equivalent constant calculation means for calculating blood vessel equivalent constants defining a relationship between blood flow velocity and blood pressure based on a blood flow velocity waveform signal and a blood pressure waveform signal output from a measurement system, which measures blood flow velocity values and blood pressure values, and a dynamic blood vessel condition calculation means for calculating blood flow velocity values under a virtual blood pressure condition, in which a load is exerted on a blood vessel using the equivalent constants to find a dynamic blood vessel condition.

2. A bypass vascular diagnosing system, comprising:

an equivalent constant calculation means for calculating bypass blood vessel equivalent constants defining a relationship between blood flow velocity and blood pressure based on a blood flow velocity waveform signal and a blood pressure waveform signal output from a measurement system, which measures blood flow velocity values and blood pressure values, and a dynamic bypass vascular condition calculation means for calculating the blood flow velocity values under a virtual blood pressure condition, in which a load is exerted on a bypass blood vessel using the equivalent constants to find a dynamic bypass vascular condition.

* * * * *